United States Patent
Leussler

(10) Patent No.: US 10,398,505 B2
(45) Date of Patent: Sep. 3, 2019

(54) MR IMAGING GUIDED THERAPY SYSTEM

(75) Inventor: Christoph Leussler, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1079 days.

(21) Appl. No.: 14/112,580

(22) PCT Filed: Apr. 2, 2012

(86) PCT No.: PCT/IB2012/051600
§ 371 (c)(1),
(2), (4) Date: Oct. 18, 2013

(87) PCT Pub. No.: WO2012/143809
PCT Pub. Date: Oct. 26, 2012

(65) Prior Publication Data
US 2014/0058248 A1    Feb. 27, 2014

(30) Foreign Application Priority Data

Apr. 21, 2011  (EP) .................................. 11163343

(51) Int. Cl.
*A61B 18/18*    (2006.01)
*A61N 5/02*    (2006.01)
(Continued)

(52) U.S. Cl.
CPC .............. *A61B 18/18* (2013.01); *A61B 5/055* (2013.01); *A61B 18/1815* (2013.01);
(Continued)

(58) Field of Classification Search
CPC combination set(s) only.
See application file for complete search history.

(56) References Cited

U.S. PATENT DOCUMENTS 4,674,481 A * 6/1987 Boddie et al. .................. 600/10
5,284,144 A * 2/1994 Delannoy .............. A61B 5/055
324/315

(Continued)

FOREIGN PATENT DOCUMENTS

| JP | 1176194 A | 3/1999 |
| JP | 2004041428 A | 2/2004 |
| WO | 2007049166 A1 | 5/2007 |

OTHER PUBLICATIONS

Chu, Xu et al "Ultra-Low Output Impedance RF Power Amplifier for Parallel Excitation", Magnetic Resonance Medicine, vol. 61, No. 4, 2009, pp. 952-961.

(Continued)

*Primary Examiner* — Jennifer Dieterle
(74) *Attorney, Agent, or Firm* — Sherry Austin

(57) ABSTRACT

The invention relates to a thermal treatment applicator (19) for the deposition of thermal energy within tissue of a body (10) of a patient. The applicator (19), comprises: a plurality of RF antennae (20) for radiating a RF electromagnetic field toward the body (10); —a plurality of RF power amplifiers (21) supplying RF signals to the RF antennae (20), wherein each RF power amplifier (21) comprises a transistor and an output matching network (22) transforming the output impedance of the transistor into a low impedance value. Moreover, the invention relates to a MR imaging guided therapy system (1).

18 Claims, 2 Drawing Sheets

(51) Int. Cl.
*A61B 5/055* (2006.01)
*A61B 18/12* (2006.01)
*A61B 18/00* (2006.01)
*A61N 5/04* (2006.01)
*A61N 5/10* (2006.01)

(52) U.S. Cl.
CPC .......... *A61N 5/025* (2013.01); *A61B 18/1206* (2013.01); *A61B 2018/0019* (2013.01); *A61B 2018/1273* (2013.01); *A61B 2018/1823* (2013.01); *A61N 5/04* (2013.01); *A61N 2005/027* (2013.01); *A61N 2005/1055* (2013.01)

(56) References Cited

U.S. PATENT DOCUMENTS

| | | | |
|---|---|---|---|
| 6,263,229 B1 | 7/2001 | Atalar | |
| 6,369,550 B1 | 4/2002 | Xiaoming et al. | |
| 6,870,868 B2 | 3/2005 | Kahen et al. | |
| 6,898,454 B2 | 5/2005 | Atalar | |
| 6,982,554 B2 | 1/2006 | Kurpad | |
| 7,048,716 B1* | 5/2006 | Kucharczyk | A61M 25/0043 600/411 |
| 7,176,686 B2* | 2/2007 | Katscher | G01R 33/5611 324/309 |
| 7,394,254 B2* | 7/2008 | Rieke | G01R 33/341 324/318 |
| 7,616,000 B2 | 11/2009 | Chu | |
| 7,692,427 B2 | 4/2010 | Lee | |
| 2004/0199070 A1* | 10/2004 | Krockel | A61N 1/403 600/412 |
| 2004/0230263 A1* | 11/2004 | Samulski | A61N 1/403 607/101 |
| 2005/0251234 A1* | 11/2005 | Kanzius et al. | 607/101 |
| 2007/0088416 A1 | 4/2007 | Atalar | |
| 2008/0228063 A1* | 9/2008 | Turner | A61N 5/02 600/411 |
| 2009/0128154 A1* | 5/2009 | Chu | G01R 33/3614 324/322 |
| 2009/0171421 A1* | 7/2009 | Atalar | A61N 1/056 607/63 |
| 2010/0010596 A1 | 1/2010 | Persson et al. | |
| 2010/0036369 A1* | 2/2010 | Hancock | A61N 5/04 606/33 |
| 2012/0169340 A1 | 7/2012 | Leussler et al. | |
| 2013/0023871 A1* | 1/2013 | Collins | 606/34 |

OTHER PUBLICATIONS

Lee et al "Radiofrequency Current Source (RFCS) Drive and Decoupling Technique for Parallel Transmit Arrays Using a High Power . . . " Magnetic Resonance in Medicine 62 p. 218-228 (2009).

* cited by examiner

MR IMAGING GUIDED THERAPY SYSTEM

CROSS-REFERENCE TO PRIOR APPLICATIONS

This application is the U.S. National Phase application under 35 U.S.C. § 371 of International Application No. PCT/IB2012/051600, filed on Apr. 2, 2012, which claims the benefit of European Patent Application No. 11163343.4, filed on Apr. 21, 2011. These applications are hereby incorporated by reference herein.

TECHNICAL FIELD

The invention relates to the field of magnetic resonance (MR) imaging. It concerns an applicator for MR imaging guided deposition of thermal energy within tissue of a body of a patient. Moreover, the invention relates to a MR imaging guided therapy system.

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

BACKGROUND OF THE INVENTION

According to the MR method in general, the body of the patient to be examined is arranged in a strong, uniform magnetic field whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse) while the magnetic field of the RF pulse extends perpendicular to the z-axis, so that the magnetization performs a precession about the z-axis. This motion of the magnetization describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°). The RF pulse is radiated toward the body of the patient via a RF coil arrangement of the MR device. The RF coil arrangement typically surrounds the examination volume in which the body of the patient is placed.

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF antennas or coils which are arranged and oriented within the examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The signal data obtained via the receiving RF antennas or coils corresponds to the spatial frequency domain and is called k-space data. The k-space data usually includes multiple lines acquired with different phase encoding. Each line is digitized by collecting a number of samples. A set of k-space data is converted to a MR image by means of Fourier transformation or by other per se known reconstruction techniques.

As described more detailed herein below, thermal energy deposition is increasingly used in medicine as a means of necrosing diseased tissues. The present invention is disclosed in the following in the context of therapeutic thermal treatment by high intensity RF irradiation. A thermal treatment applicator comprising an array of RF antennae is used for generating a RF electromagnetic field within a target zone of the body tissue to be treated. The thermal treatment applicator used in therapy is typically located outside the body over the region to be treated.

A therapeutic system comprising a thermal treatment applicator is generally known, e.g., from US 2010/0036369 A1.

In RF hyperthermia therapy the tissue of interest is irradiated with high intensity RF electromagnetic radiation which is absorbed and converted into heat, raising the temperature of the tissue. As the temperature rises above 55° C., coagulative necrosis of the tissue occurs resulting in cell death.

RF hyperthermia therapy can be advantageously combined with MR imaging, thereby enabling imaging guided local therapy. MR thermometry, based on the proton resonance frequency shift (PRFS) in water, is presently considered the 'gold standard' for the non-invasive monitoring of thermal therapies. Temperature-induced changes in the proton resonance frequency are estimated by measuring changes in phase of the acquired MR signal by means of appropriate and per se known MR imaging sequences.

In conventional thermal treatment applicators the mutual coupling of the individual RF antennae is a limiting factor for the design of optimized RF electromagnetic field characteristics. Further disadvantages of known applicator designs are significant RF power loss in feeding cables, via which the RF energy is supplied from the RF power amplifiers to the RF antennae, as well as the use of inefficient RF power amplifiers. Power efficiency of the RF power amplifiers results not only in wasted power but also in a large heat production. The heat load on the RF electronics makes the design more expensive and bulky, because provision has to be made for an appropriate cooling system, and/or negatively impacts reliability of the system.

From the foregoing it is readily appreciated that there is a need for an improved MR imaging guided therapy technique.

SUMMARY OF THE INVENTION

In accordance with the invention, a thermal treatment applicator for the deposition of thermal energy within tissue of a body of a patient is disclosed. The applicator comprises:
- a plurality of RF antennae for radiating a RF electromagnetic field toward the body;
- a plurality of RF power amplifiers supplying RF signals to the RF antennae, wherein each RF power amplifier comprises a transistor and an output matching network to supply said RF signals to the RF antenna (20) and transforming the output impedance of the transistor into a low impedance value.

The thermal treatment applicator of the invention comprises a plurality of RF antennae and a plurality of RF power amplifiers supplying RF signals to the RF antennae, wherein the RF power amplifiers are preferably associated with the RF antennae on a one-to-one basis. It is the gist of the invention to make provision for an output matching network in each RF power amplifier which transforms the output impedance of the transistor (e.g. a high power MOSFET) into a low impedance value. In this way the inter-antenna isolation within the array of RF antennae is improved. In particular for each RF amplifier there is provided its respective output matching network. Each RF power amplifier has its output coupled to its output matching network and said output network supplies the RF signal from the RF power amplifier to the RF antenna that is energised by the RF signal. Thus, the treatment applicator is provided with a multi-channel power supply, where each channel includes an RF amplifier and an output matching network and an RF antenna. In each channel, the RF amplifier in that channel supplies the RF signal via the output matching network of that channel to the RF antenna of that channel. Each channel has its proper output matching network circuited between its RF amplifier and its RF antenna. Further and each RF power amplifier is connected directly to the RF antenna via the output network associated with the respective RF power amplifier. That is the output network is directly connected to its associated RF antenna. Thus, the thermal treatment applicator of the invention has the RF antennae and its associated RF power amplifiers integrated with the output matching network in an integrated module.

A low impedance value within the meaning of the invention is significantly smaller than 50Ω. Preferably, the low impedance value corresponds to an impedance of 10 Ω or less.

Meanwhile, the output matching network matches the input impedance of each RF antenna to the optimum load of the transistor (typically 50Ω) of the respective RF power amplifier for maximizing the available output power. The approach of the invention benefits from a distinctive current-source characteristic of the RF power amplifiers, thereby exhibiting a superior robustness against load variations which is a further important advantage.

The concept of ultra-low output impedance RF power amplifiers is known per se in the context of parallel RF transmission in MR imaging (Xu Chu et al., Magnetic Resonance in Medicine, 2009, vol. 61, p. 952-961).

Typically each RF antenna of the applicator according to the invention comprises an input network for tuning and matching of the RF antenna at a given RF operation frequency. Since the output impedance of the RF power amplifiers is very low (close to zero), the input network of each RF antenna acts essentially as a parallel resonant circuit. Consequently, the current components induced in each RF antenna due to inter-antenna coupling "see" a large impedance and are thereby substantially suppressed.

According to a preferred embodiment of the invention, each RF power amplifier is connected directly to the RF antenna associated with the respective RF power amplifier. A direct connection means that the RF power amplifiers are actually located "on" the applicator, i.e. the RF antennae as well as the RF power amplifiers are integral components of a unit constituting the thermal treatment applicator of the invention. It is essential that the RF amplifiers are located near the RF antennae, whereby inter-antenna coupling is further reduced. Moreover, the required RF power can be reduced because lossy cable connections between the RF power amplifiers and the associated RF antennae are avoided. In any case, the length of the connection between the RF power amplifiers and the respective RF antennae should be significantly less than half the wavelength of the RF signals at the RF operation frequency of the applicator.

In order to be usable in image guided therapy, the thermal treatment applicator of the invention should be MR imaging compatible and/or transparent in X-ray examinations. The use of ferromagnetic materials should be avoided in the design of the applicator. Moreover, materials should be selected which absorb X-ray radiation only to a small extent.

According to another preferred embodiment of the invention, the thermal treatment applicator further comprises RF traps connected to the RF antennae, which RF traps are tuned to the MR resonance frequency of a MR device which is used in combination with the applicator. In this way, the absorption of RF energy radiated by the MR device for excitation and/or manipulation of magnetic resonance in the applicator is minimized. Furthermore, the RF antenna preferably comprises PIN diode switches. In this way, the RF antennae of the applicator are made transparent to the RF field generated by the MR device. PIN diode switches should be used in the RF antennae of the applicator in case the MR resonance frequency of the MR device is close to the RF operation frequency of the applicator.

According to yet another preferred embodiment of the invention, the applicator further comprises one or more controllable signal generators generating RF signals which are supplied to the inputs of the RF power amplifiers. In this embodiment all RF components required for the deposition of thermal energy within the body tissue are integrated into a single unit. The controllable signal generator enables the control of the RF field distribution within the target zone irradiated by the RF antennae array. To this end, the controllable signal generator should be configured to control the amplitude and phase of each RF signal supplied to the individual RF power amplifiers. For external control of the thermal treatment applicator, for example via the back-end electronics of a MR device used in combination with the applicator, an optical link may be sufficient. A battery may be used as energy supply for the controllable signal generator and the RF power amplifiers.

The applicator may further comprise a feedback loop formed by a pick-up antenna for picking up electromagnetic radiation from a target zone irradiated by the RF antennae, which pick-up antenna is connected to the controllable signal generator. The pick-up antenna works as a sensor element which detects the amplitude of the RF electromagnetic field generated within the target zone. In this way, overheating of the treated tissue can be avoided and load variations can be compensated for automatically.

In a further preferred embodiment of the invention, the RF power amplifiers of the applicator are class-D, class-E, or class-F switching amplifiers. Such switching amplifiers have a high-power efficiency due to the fact that principally a perfect switching operation does not dissipate power. This advantage is beneficial for the RF power amplifiers in the applicator according to the invention though switching amplifiers are characterized by an extremely high non-linearity. The linearity of the RF amplification is of minor importance for the generation of the RF electromagnetic fields for deposition of thermal energy.

Preferably, the applicator of the invention operates in a RF frequency range of 50-200 MHz. This frequency range is appropriate for generating regional hyperthermia in deep tissue regions.

According to yet another preferred embodiment of the invention, the RF antennae are interconnected by decoupling networks for further reducing mutual coupling of the RF antennae. For example, capacitive or inductive decoupling bridges or appropriate multi-port networks interconnecting the RF antennae may be used in practice.

The invention does not only relate to a thermal treatment applicator, but also to a MR imaging guided therapy system. The system comprises:

- at least one main magnet coil for generating a uniform, steady magnetic field within an examination volume,
- a number of gradient coils for generating switched magnetic field gradients in different spatial directions within the examination volume,
- at least one RF coil for generating RF pulses at a MR resonance frequency within the examination volume and/or for receiving MR signals from a body of a patient positioned in the examination volume,
- a control unit for controlling the temporal succession of RF pulses and switched magnetic field gradients,
- a reconstruction unit for reconstructing a MR image from the received MR signals;
- a thermal treatment applicator of the type specified above.

The thermal treatment applicator according to the invention can advantageously be used in combination with most MR imaging devices presently being used in clinical practice, wherein the thermal treatment applicator may be located within the examination volume of the MR device. The interconnection of the thermal treatment applicator and the back-end electronics of the MR device can be established, for example, via an optical link. Preferably, the thermal treatment applicator operates at a RF frequency which is different from the MR resonance frequency. In this way, interferences between the operation of the thermal treatment applicator and the MR examination are avoided.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
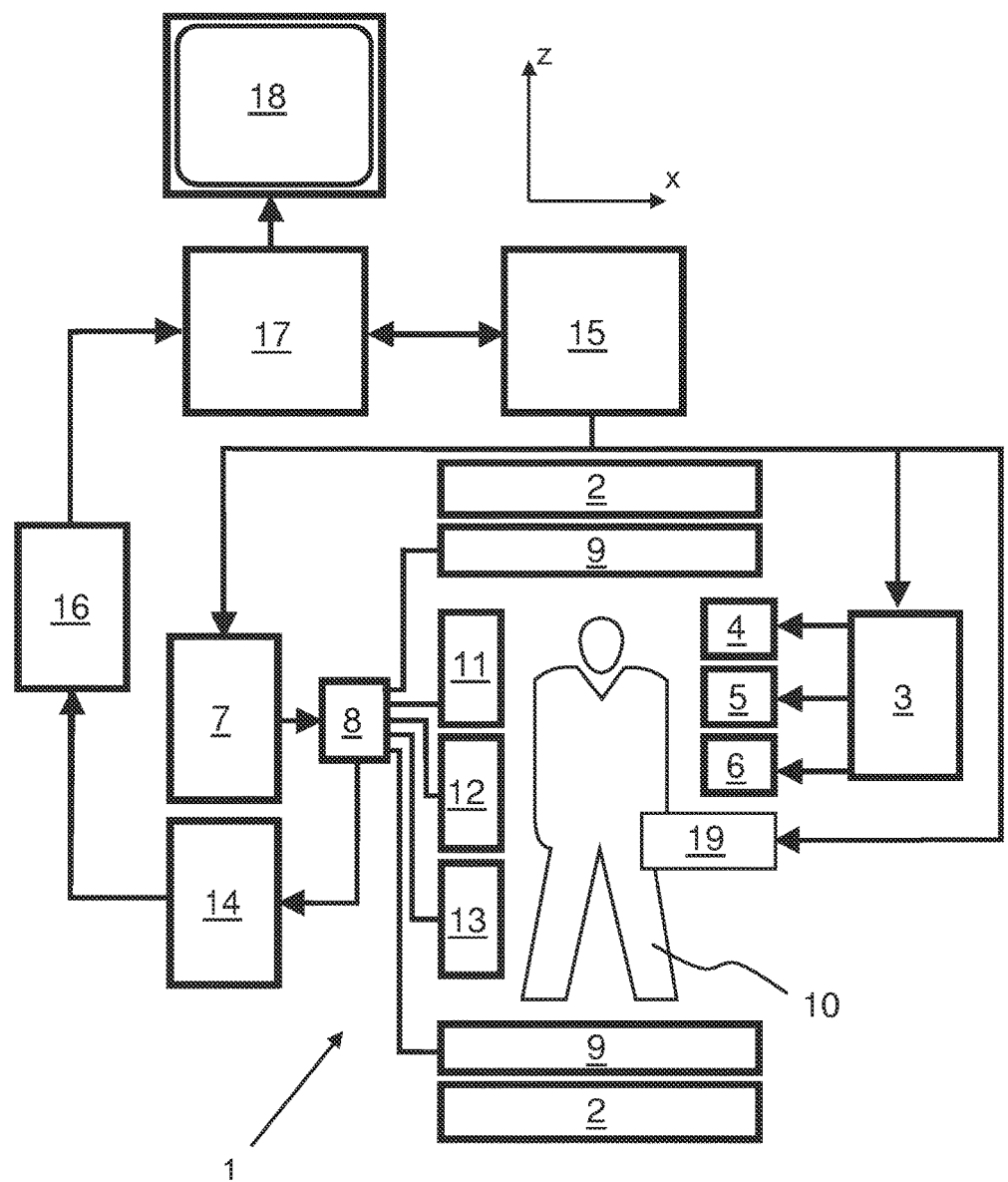
FIG. 1 shows a MR imaging guided therapy system according to the invention.

With reference to FIG. 1, a MR imaging guided therapy system 1 is shown. The system comprises superconducting or resistive main magnet coils 2 such that a substantially uniform, temporally constant main magnetic field is created along a z-axis through an examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a whole-body volume RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the whole-body volume RF coil 9.

For generation of MR images of limited regions of the body 10, a set of local array RF coils 11, 12, 13 are placed contiguous to the region selected for imaging. The array coils 11, 12, 13 can be used for parallel imaging to receive MR signals induced by body-coil RF transmissions.

The resultant MR signals are picked up by the whole body volume RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a appropriate reconstruction algorithms. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

A thermal treatment applicator 19 for deposition of thermal energy within the tissue of the body 10 is located within the examination volume. The thermal treatment applicator 19 is controlled via the control unit 15 of the depicted MR imaging guided therapy system 1.

Figure 2:
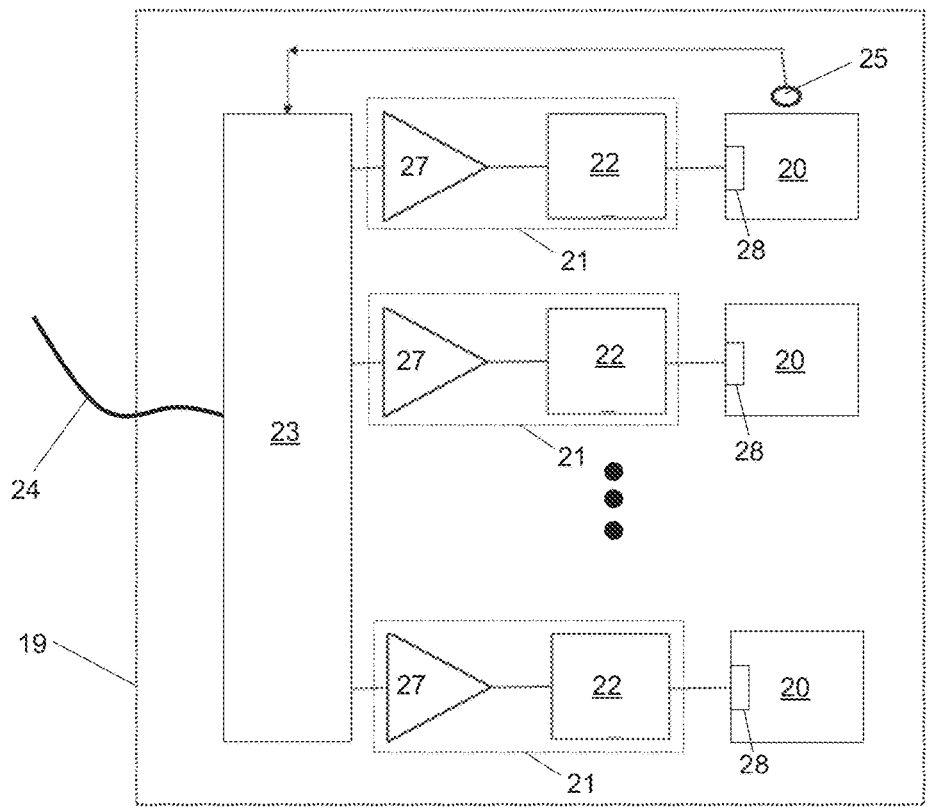
FIG. 2 shows a block diagram of a thermal treatment applicator according to the invention.
Figure 3:
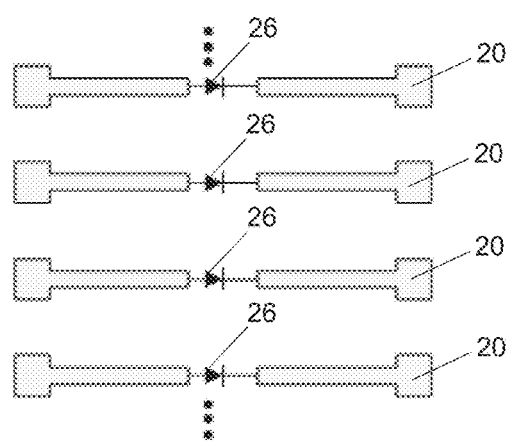
FIG. 3 schematically shows an embodiment of an array of RF antennae of a thermal treatment applicator according to the invention.

With continuing reference to FIG. 1 and with further reference to FIGS. 2 and 3, embodiments of the thermal treatment applicator 19 are described.

The thermal treatment applicator 19 comprises a plurality of RF antennae 20 for radiating a RF electromagnetic field toward the body 10. The RF electromagnetic radiation is absorbed in the tissue of the body 10 and converted into heat. The spatial distribution of the generated RF electromagnetic field is determined by the design of the array of the RF antennae 20 and by the amplitudes and phases of RF signals provided to the individual RF antennae 20.

The thermal treatment applicator 19 comprises RF power amplifiers 21, wherein each RF power amplifier 21 comprises a transistor 27 (typically a high-power MOSFET). An output matching network 22 of each RF power amplifier 21 transforms the output impedance of the respective transistor 27 into a low impedance value. The RF power amplifier (21), including the output matching network (22), and the RF antenna (20) coupled to that output matching network form a channel. FIG. 2 thus shows a multi-channel power supply for the RF antennae (20). Simultaneously, the output matching network 22 matches the input impedance of the respective RF antenna 20 to the optimum load of the transistor 27 of the RF power amplifier 21. In this way, the mutual coupling of the RF antennae 20 is minimized and the available output power of the RF power amplifiers 21 and, hence, their power efficiency is maximized. Each RF antenna 20 comprises an input matching network 28 for tuning and matching of the RF antenna 20 at a given RF operation frequency of the thermal treatment applicator 19. When the impedance at the output of the output matching network 22 is low (close to zero), the input matching network 28 of the respective RF antenna 20 acts as a parallel resonant circuit, and the currents induced due to inter-antenna coupling "see" a large impedance and are thereby substantially suppressed.

Provision is made for a controllable signal generator 23 which supplies RF signals to the individual RF power amplifiers 21. The phases and amplitudes of the RF signals are controllable by means of the signal generator 23 in order to enable control of the spatial distribution of the RF electromagnetic field radiated via the array of RF antennae 20. For generation of the RF signals the controllable signal generator 23 may for example comprise appropriate direct digital synthesizers (DDS). The controllable signal generator 23 is connected to the back-end electronics (e.g., host computer 15) of the MR imaging guided therapy system 1 via an optical link 24.

Moreover, the thermal treatment applicator 19 comprises a feedback loop formed by a pick-up antenna 25 (for example a loop antenna). The pick-up antenna 25 picks up electromagnetic radiation from the target zone irradiated by the RF antennae 20. The pick-up antenna 25 is connected to the controllable signal generator 23. This enables automatic feedback control in order to avoid overheating of the treated tissue and to compensate for load variations (for example due to different patient anatomies). The individual RF antennae 20 are made transparent to the RF fields generated for MR imaging by using PIN diode switches 26. In this way the thermal treatment applicator 19 is usable even in case the MR resonance frequency is close to the RF operation frequency of the thermal treatment applicator 19.

According to a further embodiment of invention, which is not depicted in the Figures, the thermal treatment applicator 19 and the at least one RF coil 9 are integrated in a shared housing. In this embodiment, the (local) RF coils for excitation and/or acquisition of MR signals as well as the RF antennae of the thermal treatment applicator constitute a single integrated unit. The RF coils are used for picking up MR signals directly from the body region locally treated by means of the thermal treatment applicator.

In summary, properly designed output matching networks are applied at the output stages of the RF amplifiers according to the invention. The output matching networks transform the output impedance of the transistors of the RF power amplifiers into a low value, and simultaneously maximize the available output power by establishing an optimal load for the respective transistor (typically 50Ω). In combination with the input matching networks of the RF antennae, the RF power amplifiers of the invention act as current sources, and the current variations due to mutual coupling of the RF antennae and due to load variations are more or less completely suppressed. The invention thus facilitates the optimization of the RF transmit performance of the thermal treatment applicator by eliminating constraints on the array geometry of the RF antennae. The integration of the RF amplifiers into the applicator unit further reduces mutual couplings and improves the power efficiency of the generation of RF radiation because the RF amplifiers are located closely to the RF antenna elements. The required RF power is reduced. Consequently smaller and cheaper RF power electronics can be used.

The invention claimed is:

1. A thermal treatment applicator for deposition of thermal energy within tissue of a body of a patient in a radio frequency field generated by a magnetic resonance device, the thermal treatment applicator comprising:
  a plurality of radio frequency antennae configured to radiate a radio frequency electromagnetic field toward the body; and
  a plurality of radio frequency power amplifiers configured to supply radio frequency signals to the radio frequency antennae, respectively, each radio frequency power amplifier comprising a transistor and an output matching network configured to supply said radio frequency signals to the respective radio frequency antenna and to transform an output impedance of the transistor into a low impedance value,
  wherein the radio frequency power amplifiers are connected directly to the radio frequency antennae via the output matching networks respectively associated with the radio frequency power amplifiers, and wherein the radio frequency power amplifiers and the radio frequency antennae are integrated within an integrated module, and
  wherein each radio frequency antenna comprises a PIN diode switch for selectively connecting to the respective radio frequency power amplifier within the integrated module.

2. The applicator of claim 1, wherein each radio frequency antenna comprises an input network for tuning and matching of the radio frequency antenna at a given radio frequency operation frequency of the applicator.

3. The applicator of claim 1, wherein the RF antennae of the applicator are transparent to the radio frequency field generated by the magnetic resonance device by operation of the PIN diodes, respectively.

4. The applicator of claim 1, further comprising radio frequency traps connected to the radio frequency antennae, respectively, the radio frequency traps being tuned to a magnetic resonance frequency of the magnetic resonance device.

5. A thermal treatment applicator for deposition of thermal energy within tissue of a body of a patient in a magnetic resonance device, the thermal treatment applicator comprising:

a plurality of radio frequency antennae configured to radiate a radio frequency electromagnetic field toward the body; and a plurality of radio frequency power amplifiers configured to supply radio frequency signals to the radio frequency antennae, respectively, each radio frequency power amplifier comprising a transistor and an output matching network configured to supply said radio frequency signals to the respective radio frequency antenna and to transform an output impedance of the transistor into a low impedance value, wherein the radio frequency antennae comprise PIN diode switches selectively connecting to the radio frequency power amplifiers via the output matching networks respectively associated with the radio frequency power amplifiers.

6. The applicator of claim 1, further comprising one or more controllable signal generators generating radio frequency signals supplied to inputs of the radio frequency power amplifiers, respectively.

7. The applicator of claim 6, comprising a feedback loop formed by a pick-up antenna for picking up electromagnetic radiation from a target zone irradiated by the radio frequency antennae, the pick-up antenna being connected to the controllable signal generator.

8. The applicator of claim 1, wherein the radio frequency power amplifiers are class-D, class-E, or class-F switching amplifiers.

9. The applicator of claim 1, wherein the applicator operates in a radio frequency range of 50-200 MHz.

10. The applicator of claim 1, wherein the radio frequency antennae are interconnected by decoupling networks for mutual decoupling of the radio frequency antennae.

11. A magnetic resonance imaging guided therapy system comprising:
    at least one main magnet coil for generating a uniform, steady magnetic field within an examination volume;
    a plurality of gradient coils configured to generate switched magnetic field gradients in different spatial directions within the examination volume;
    at least one radio frequency coil configured to at least one of generating radio frequency pulses at a magnetic resonance frequency within the examination volume or receiving magnetic resonance signals from a body of a patient positioned in the examination volume;
    a host computer configured to control a temporal succession of radio frequency pulses and switched magnetic field gradients;
    a image reconstruction processor configured to reconstruct a magnetic resonance image from the received magnetic resonance signals; and
    a thermal treatment applicator configured to provide thermal energy within tissue of the body of the patient, the thermal treatment applicator comprising:
        a plurality of radio frequency antennae configured to radiate a radio frequency electromagnetic field toward the body; and
        a plurality of radio frequency power amplifiers configured to supply radio frequency signals to the radio frequency antennae, respectively, each radio frequency power amplifier comprising a transistor and an output matching network configured to supply the radio frequency signals to the respective radio frequency antenna and to transform an output impedance of the transistor into a low impedance value,
        wherein the radio frequency power amplifiers are selectively connectable to the radio frequency antennae via the output matching networks respectively and PIN diode switches associated with the radio frequency power amplifiers, and wherein the radio frequency power amplifiers and the radio frequency antennae are integrated with in an integrated module, making the thermal treatment applicator transparent to a radio frequency field generated by the magnetic resonance device.

12. The system of claim 11, wherein the thermal treatment applicator is located within the examination volume.

13. The system of claim 11, wherein the thermal treatment applicator is connected to the host computer via an optical link.

14. The system of claim 11, wherein the thermal treatment applicator operates at a radio frequency which is different from the magnetic resonance frequency.

15. The system of claim 11, wherein the thermal treatment applicator and the at least one radio frequency coil are integrated in a shared housing.

16. The applicator of claim 1, wherein each of the connections between the radio frequency amplifiers and the respective radio frequency antennae is less than half a wavelength of the radio frequency signals at the radio frequency operation frequency of the applicator.

17. The applicator of claim 6, wherein the one or more controllable signal generators are integrated within the integrated module, along with the radio frequency power amplifiers and the radio frequency antennae.

18. The applicator of claim 5, wherein the PIN diode switches make the applicator transparent to a radio frequency field generated by the magnetic resonance device.

* * * * *